US005814599A

United States Patent [19]

Mitragotri et al.

[11] Patent Number: 5,814,599
[45] Date of Patent: Sep. 29, 1998

[54] TRANSDERMAL DELIVERY OF ENCAPSULATED DRUGS

[75] Inventors: Samir S. Mitragotri, Cambridge; Daniel Blankschtein, Brookline; Robert S. Langer, Newton, all of Mass.

[73] Assignee: Massachusetts Insitiute of Technology, Cambridge, Mass.

[21] Appl. No.: 511,583

[22] Filed: Aug. 4, 1995

[51] Int. Cl.[6] .............................. A61K 38/28; A61N 1/30; A61M 37/00; A61M 31/00
[52] U.S. Cl. ............................ 514/3; 604/20; 604/23; 604/49; 604/304; 604/892.1; 128/24; 128/632; 128/633; 128/760; 128/761; 424/450
[58] Field of Search ....................... 604/20–23, 49, 604/304, 892.1, 290; 128/24, 632, 633, 760, 771; 424/450; 514/3

[56] References Cited

U.S. PATENT DOCUMENTS

| | | | |
|---|---|---|---|
| 3,551,554 | 12/1970 | Herschler | 424/7 |
| 3,711,602 | 1/1973 | Herschler | 424/45 |
| 3,711,606 | 1/1973 | Herschler | 424/243 |
| 4,002,221 | 1/1977 | Buchalter | 181/0.5 |
| 4,127,125 | 11/1978 | Takemoto et al. | 128/172.1 |
| 4,144,646 | 3/1979 | Takemoto et al. | 32/40 R |
| 4,176,664 | 12/1979 | Kalish | 128/156 |
| 4,249,531 | 2/1981 | Hiller et al. | 128/260 |
| 4,280,494 | 7/1981 | Cosgrove, Jr. et al. | 128/213 R |
| 4,309,989 | 1/1982 | Fahim | 128/24 A |
| 4,372,296 | 2/1983 | Fahim | 128/24 A |
| 4,537,776 | 8/1985 | Cooper | 514/424 |
| 4,557,943 | 12/1985 | Rosler et al. | 427/38 |
| 4,563,184 | 1/1986 | Korol | 604/368 |
| 4,646,725 | 3/1987 | Moasset | 128/24 A |
| 4,698,058 | 10/1987 | Greenfeld et al. | 604/266 |
| 4,767,402 | 8/1988 | Kost et al. | 604/22 |
| 4,780,212 | 10/1988 | Kost et al. | 210/646 |
| 4,820,720 | 4/1989 | Sanders et al. | 514/356 |
| 4,821,740 | 4/1989 | Tachibana et al. | 128/798 |
| 4,834,978 | 5/1989 | Nuwayser | 424/448 |
| 4,855,298 | 8/1989 | Yamada et al. | 514/259 |
| 4,860,058 | 8/1989 | Kobayashi et al. | 355/27 |
| 4,863,970 | 9/1989 | Patel et al. | 514/784 |
| 4,953,565 | 9/1990 | Tachibana et al. | 128/798 |
| 5,006,342 | 4/1991 | Cleary et al. | 424/445 |
| 5,007,438 | 4/1991 | Tachibana et al. | 128/798 |
| 5,016,615 | 5/1991 | Driller | 128/24 A |
| 5,076,273 | 12/1991 | Schoendorfer et al. | 128/632 |
| 5,115,805 | 5/1992 | Bommannan et al. | 128/24 AA |
| 5,139,023 | 8/1992 | Stanley et al. | 128/637 |
| 5,140,985 | 8/1992 | Schroder et al. | 128/632 |
| 5,171,215 | 12/1992 | Flanagan | 604/22 |
| 5,197,946 | 3/1993 | Tachibana | 604/22 |
| 5,231,975 | 8/1993 | Bommannan et al. | 128/24 AA |
| 5,267,985 | 12/1993 | Shimada et al. | 604/290 |
| 5,315,998 | 5/1994 | Tachibana et al. | 128/660.01 |
| 5,323,769 | 6/1994 | Bommannan et al. | 601/2 |
| 5,386,837 | 2/1995 | Sterzer | |
| 5,401,237 | 3/1995 | Tachibna et al. | 604/4 |
| 5,405,614 | 4/1995 | D'Angelo et al. | 424/449 |
| 5,415,629 | 5/1995 | Henley | |
| 5,421,816 | 6/1995 | Lipkovker | 604/20 |
| 5,445,611 | 8/1995 | Eppstein et al. | 604/49 |
| 5,458,140 | 10/1995 | Eppstein et al. | 128/632 |
| 5,580,575 | 12/1996 | Unger et al. | 424/450 |

FOREIGN PATENT DOCUMENTS

| | | |
|---|---|---|
| 0043738 B1 | 10/1985 | European Pat. Off. . |
| 386408 A2 | 5/1990 | European Pat. Off. . |
| 612525 A1 | 8/1994 | European Pat. Off. . |
| 27 56 460A1 | 6/1979 | Germany . |
| 3-170172 | 7/1991 | Japan . |
| 445433 | 11/1974 | U.S.S.R. . |
| 556805 | 6/1977 | U.S.S.R. . |
| 591186 | 1/1978 | U.S.S.R. . |
| 0910157 | 2/1978 | U.S.S.R. . |
| 506421 | 2/1978 | U.S.S.R. . |
| 1 577 551 | 2/1976 | United Kingdom . |
| 2153223 | 8/1985 | United Kingdom . |
| WO 88/0000 | 11/1988 | WIPO . |
| WO 90/01971 | 3/1990 | WIPO . |
| WO 91/12772 | 9/1991 | WIPO . |
| WO 93/20745 | 10/1993 | WIPO . |

OTHER PUBLICATIONS

Egorov, E.A. et al., "Use of the Variants of the Pharmacophysical Influence in Ophthalmology", 102 Ophthalmology Journal #2 (1992).

Eppstein, D.A. et al., "Applications of Liposome Formulations for Antimicrobial/Antiviral Therapy" Liposomes as Drug Carriers 311, 315 (G. Gregoriadis ed. 1988).

Eppstein, D.A., "Medical Utility of Inteferons: Approaches to Increasing Therapeutic Efficacy" 7 Pharmacy International 195–198 (1986).

Eppstein, D.A. et al., "Alternative Delivery Systems for Peptides and Proteins as Drugs" 5 CRC Reviews in Therapeutic Drug Carrier Systems 99, 125 (1988).

Loshilov, V.I. et al., "Research of the Technological Process of Ultrasound Treatment of Infected Wounds" (1976).

Ulashik, V.S. et al., Ultrasound Therapy (Minsk, Belarus 1983).

Remington Phamaceutical Sciences, pp. 267–272, 1600–1606, 1614, 1690–1693, 1990.

D.A. Jones, Polymeric Carriers for Active Agents in Transdermal and Related Drug Delivery Systems, Noyes Data Corporation, pp. 223–279, 1984.

(List continued on next page.)

Primary Examiner—Cecilia J. Tsang
Assistant Examiner—Jennifer Harle
Attorney, Agent, or Firm—Arnall Golden & Gregory LLP

[57] ABSTRACT

Applications of low-frequency (20 KHz) ultrasound enhances transdermal transport of high-molecular weight proteins. This method includes a simultaneous application of ultrasound and protein on the skin surface in order to deliver therapeutic doses of proteins across the skin. Examples demonstrate in vitro and in vivo administration of insulin (molecular weight 6,000 D), and in vitro administration of gamma interferon (molecular weight 17,000 D), and erythropoeitin (molecular weight 48,000 D).

9 Claims, 4 Drawing Sheets

OTHER PUBLICATIONS

Schreier, et al., Liposomes and Niosomes as Topical Drug Carriers: Dermal and Transdermal Drug Delivery, Journal of Controlled Release, vol. 30, pp. 1–15, 1994.

Kamath, et al., Biodegradable Hydrogels in Drug Delivery, Advanced Drug Delivery Reviews, vol. 11, pp. 59–84, 1993.

Domb, et al., Polyanhydrides—Synthesis and Characterization, Advances in Polymer Science, vol. 107 pp. 93–141, 1993.

Agrawal, et al., the Effects of Ultrasound Irradiation on a Biodegradable 50–50% Copolymer of Polylactic and Polyglycolic Acids, Journal of Biomedical Research, vol. 28, No. 8, pp. 851,859, Aug. 1994.

Smith, et al., Percutaneous Penetration Enhancers, I.E.C., Lyon, France, pp. 369–382, 1995.

Bhat, et al., Optimization of Delivery of Betamethasone–dipropionate from Skin Preparation, Indian Drugs, 32/5, pp. 211–5, pp. 211–214, 1995.

Apfel, R. F., "Possibility of Microcavitation from Diagnostic Ultrasound," *IEEE Trans. Ultrason. Ferroelectrics Freq. Control* UFFC–33:139–142 (1986).

Aungst, et al., "Contributions of Drug Solubilization, Partitioning, Barrier Disruption, and Solvent Permeation to the Enhancement of Skin Permeation of Various Compounds with Fatty Acids and Amines," *Pharm. Res.* 7:712–718 (1990).

Barry, "Mode of Action of Penetration Enhancers in Human Skin," *J. Controlled Rel.* 6:85–97 (1987).

Bommer, et al., "Subcutaneous Frythropoeitin," *Lancet* 406 (1988).

Burnette, R. R., "Iontophoresis," *Transdermal Drug Delivery Developmental Issues and Research Initiatives* (Hadgraft and Guy, Editors, Marcel Dekker, 247–291, 1989).

Cleary, Gary W., "Transdermal Controlled Release Systems, "Medical Applications of Controlled Release (Langer and Wise, Editors, CRC Press 203–251, 1984).

Clegg and Vaz, "Translational diffusion of proteins and lipids in artificial lipid bilayer membranes. A comparison of experiment with theory," *Progress in Protein–Lipid Interactions* Watte, ed. (Elsvier, NY 1985) Chapter 5:173–229.

Davis, J., et al., "Characterization of Recombinant Human Erythropoietin Produced in Chinese Hamster Ovary Cells," *Biochemistry* 26:2633–2638 (1987).

Ebert, et al., "Transbuccal Absorption of Diclofenac Sodium in a Dog Model," *Controlled Release Technology Pharmaceutial Application* (Lee, et al. Editors, American Chemical Society)310–321 (1987).

Eggerth, et al., "Evaluatin of Hamster Cheek Pouch as a Model for Buccal Absorption," *Proceed. Intern. Symp. Rel. Bioact. Mater.,*(Controlled Release Society, Inc.) 14:180–181 (1987).

D'Emanuele, et al., "An Investigation of the Effects of Ultrasound on Degradable Polyanhydride matrices," *Macromolecules* 25:511–515 (1992).

Elias, "The Microscopic Structure of the Epidermis and Its Derivatives," *Percutaneous Absorption: Mechanisms–Methodology–Drag Delivery* (Bronaugh, R. L., Maibach, H., Editors, Marcel Dekker, New York,) 1–12 (1989).

Flynn, G. L., "Mechanism of Percutaneous Absorption from Physicochemical Evidence," *Percutaneous Absorption: Mechanisms–Methodology–Drug Delivery* (Bronaugh, R. L., Maibach, H., Editors, Marcel Dekker, New York) 27–51 (1989).

Friedman, R. M., '*Interfrons: A Primer*', (Academic Press, New York, 1981).

Gaertner, W., "Frequency Dependence of Ultrasonice Cavitation," *J. Acoust. Soc. Am.* 26:977–980 (1954).

Ghanem et al., "The effects of ehtanol on the transport of lipophilic and polar permeants across hairless moust skin: Methods/validation of a novel approach," *Int. J. Pharm.* 78:137–156 (1992).

Grups and Frohmuller, "Cyclic Interferon Gamma Treatment of Patients with Metastatic Renal Carcinoma," *J. Med.* 64(3):218–220 (1989).

Junginger, et al., "Visualization of Drug Transport Across Human Skin and the Influence of Penetration Enhancers," *Drug Permeation Enhancement* (Hsieh, D.S., Editors, Marcel Dekker, Inc. New York) 59–89 (1994).

Kasting, et al., "Prodrugs for Dermal Delivery: Solubility, Molecular Size, and Functional Group Effects," Prodrugs: Topical and Ocular Delivery Sloan, ed. (Marcel Dekker, NY 1992) 117–161.

Kost and Langer, "Ultrasound–Mediated Transdermal Drug Delivery," *Topical Drug Bioequivalence and Penetration* (Maibach, H. I., Shah, V. P., Editors, Plenum Press, New York) 91–104 (1993).

Lee, V. H. L., et al., "Protase Inhibition as an Additional Mechanism for the Nasal Absorption Enhancement Effect of Sodim Taurodihydrofusidate," *Proceed. Intern. Symp. Control. Rel. Bioact. Mater* 14:55–56 (1987).

Lee, V. H. L., et al., "Nasal Peptide and Protein Absorption Promotors: Aminopeptidase Inhibition as a Predictor of Absorption Enhancement Potency of Bile Salts," *Proceed. Intern. Symp. Control. Rel. Bioact. Mater* 14:53–54 (1987).

Levy, et al., "Effect of Ultrasound on Transdermal Drug Delivery to Rats and Guinea Pigs," *J. Clin. Invest.* 83:2074–2078 (1989).

Liu, et al., "Cotransport of Estradiol and Ethanol Through Human Skin In Vitro: Understanding the Permeant/Enhancer Flux Relationship," *Pharmaceutical Research* 8:938–944 (1991).

Liu, et al., "Experimental Approach To Elucidate the Mechanism of Ultrasound–Enhanced Polymer Erosion and Release of Incorporated Substances," *Macromolecules* 25:123–128 (1992).

Machluf and Kost, "Ultrasonically enhanced transdermal drug delivery, Experimental approaches to elucidate the mechanism," *J. Biomater. Sci. Polymer Edn.* 5:147–156 (1993).

Mark, et al., "Oleic Acid Concentration and Effect in Human Stratum Corneum: Non–Invasive Determination by Attenuated Total Reflectance Infrared Spectroscopy In Vivo," *J. Controlled Rel.* 12:67–75 (1990).

Mitragotri, et al., "Ultrasound–Mediated Transdermal Protein Delivery," *Science* 259:850–853 (1995).

Mitragotri, et al., "A Mechanistic Study of Ultrasonically–Enhanced Transdermal Drug Delivery," *J. Pharm. Sci.* 84:697–706 (1995).

Morimoto, Y., et al., "Prediction of Skin Permeability of Drugs: Comparison of Human and Hairless Rat Skin," *J. Pharm. Pharmacol.* 44:634–639 (1991).

Nagai and Konishi, "Buccaal/Gingival Drug Delivery Systems," *Journal of Controlled Release* (Elsevier Science Publishers B.V.,k Amsterdam) 6:353–360 (1987).

Newman, J., et al., "Hydrocortisone Phonophoresis," *J. Am. Pod. Med. Assoc.* 82:432–435 (1992).

Olanoff and Gibson, "Method to Enhance Intranasal Peptide Delivery," *Controlled Release Technology Pharmaceutical Application* (Lee, et al. Editors, American Chemical Society).

Ongpipattanankul, et al., "Evidence that Oleic Acid Exists in a Separate Phase Within Stratum Corneum Lipids," *Pharm. Res.* 8:350–354 (1991).

Parkin, et al., "Atopic manifestations in the acquired immune deficiency syndrome: response to recombinant interferon gamme," *Br. Med. J.,* 294:1185–1186 (1987).

Pishko, et al., "Amperometric Glucose Microelectrodes Prepared through Immobilization of Glucose Oxidase in Redox Hydrogels," *Anal. Chem.* 63:2268–2272 (1991).

Potts and Guy, "Predicting Skin Permeability," *Pharm. Res.* 9:663–669 (1992).

Prausnitz, et al., "Electroporation of mammalian skin: A mechanism to enhance transdermal drug delivery," *Proc. Natl. Acad. Sci.USA* 90:10504–10508 (1993).

Quillen, W.S., "Phonophoresis: A Review of the Liternature and Technique," *Athl. Train.* 15:109–110 (1980).

Robinson & Lee, "Influence of Drug Properties on Design," *Controlled Drug Delivery* 42–43.

Rosell, J., et al., "Skin Impedance From 1 Hz to 1 MHz," *IEEE Trans. Biomed. Eng.* 35:649–651 (1988).

Skauen, et al., "Phonophoresis," *Int. J. Pharm.* 20:235–245 (1984).

Tamada, et al., *Proceed. Intern. Symp. Control. Res. Bioact. Mater.* 22, 129–130 (1995).

Tocanne, et al., "Lipid lateral diffusion and membrane organization," *FEB* 257:10–16 (1989).

Tyle and Agrawala, "Drug Delivery by Phonophoresis," *Pharm. Res.* 6:355–361 (1989).

Walker and Hadgraft, "Oleic acid—a membrane 'fluidiser' or fluid within the membrane," *Int. J. Pharm.* 71:R1–R4 (1991).

Walmsley, "Applications of Ultrasound in Dentistry," *Ultrasound in Med. and Biol.* 14:7–14 (1988).

Walters, K. A., "Penetration Enhancers and Their Use in Transdermal Therapeutic Systems," *Transdermal Drug Delivery: Developmental Issues and Research Initiatives,* 197–246 (Hadgraft J., Guy, R.H., Editors, Marcel Dekker, 1989).

Wester and Mailbach, "Animal Models for Percutaneous Absorption," *Topical Drug Bioavailability Bioequivalance and Penetration* (Shah and Maibach, Editors, Plenum Press, New York) 333–349, (1993).

Wheatley, et al., "Use of Ussing Chamber for Investigation of Drug Delivery Across Viable Nasal Tissue Membranes," *Proceed. Intern. Symp. Control. Rel. Bioact. Mater.* (Controlled Release Society, Inc. 14:26–27 (1987).

Williams, et al., "On the non–Gaussian distribution of human skin permeabilities," *Int. J. Pharm.* 86:69–77 (1992).

Wilschut, et al., "Estimating Skin Permeation, The Validation of Five Mathematical Skin Permeation Models," *Chemosphere* 30:1275–1296 (1995).

FIG. 4

TRANSDERMAL DELIVERY OF ENCAPSULATED DRUGS

BACKGROUND OF THE INVENTION

The present invention is generally in the area of drug delivery, and is particularly an improved method for transdermal drug delivery.

The United States government has rights in this invention by virtue of NIH grant GM44884 to R. Langer.

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, In *Percutaneous Absorption: Mechanisms-Methodology-Drag Delivery.,* Bronaugh, R. L., Maibach, H. 1. (Ed), pp 1–12, Marcel Dekker, New York, 1989. The word "transdermal" is used herein as a generic term. However, in actuality, transport of drugs occurs only across the epidermis where the drug gets absorbed in the blood capillaries. When compared to injections, TDD eliminates the associated pain and the possibility of infection. Theoretically, the transdermal route of drug administration could be advantageous in the delivery of many therapeutic proteins, because proteins are susceptible to gastrointestinal degradation and exhibit poor gastrointestinal uptake, proteins such as interferons are cleared rapidly from the blood and need to be delivered at a sustained rate in order to maintain their blood concentration at a high value, and transdermal devices are easier to use than injections.

In spite of these advantages, very few drugs and no proteins or peptides are currently administered transdermally for clinical applications because of the low skin permeability to drugs. This low permeability is attributed to the stratum corneum (SC), the outermost skin layer which consists of flat, dead cells filled with keratin fibers (keratinocytes) surrounded by lipid bilayers. The highly-ordered structure of the lipid bilayers confers an impermeable character to the SC (Flynn, G. L., In *Percutaneous Absorption: Mechanisms-Methodology-Drug Delivery.;* Bronaugh, R. L., Maibach, H. I. (Ed), pages 27–53, Marcel Dekker, New York, 1989). Several methods, which include chemical enhancers (Burnette, R. R. In *Developmental Issues and Research Initiatives;* Hadgraft J., G., R. H., Eds., Marcel Dekker: 1989; pp. 247–288) and electricity (Prausnitz *Proc. Natl. Acad. Sci.USA* 90, 10504–10508 (1993); Walters, K. A., in *Transdermal Drug Delivery: Developmental Issues and Research Initiatives*, Ed. Hadgraft J., Guy, R. H., Marcel Dekker, 1989), have been proposed to enhance transdermal drug transport. However, the efficacy of these methods in enhancing transdermal protein transport has been limited by the large protein size and relatively low electric charge on the proteins.

Ultrasound has been shown to enhance transdermal transport of low-molecular weight drugs (molecular weight less than 500) across human skin, a phenomenon referred to as sonophoresis (Levy, J. Clin Invest. 1989, 83, 2974–2078; Langer, R., In *"Topical Drug Bioavailability, Bioequivalence, and Penetration"*; pp. 91–103, Shah V. P., M.H.I., Eds. (Plenum: New York, 1993); Frideman, R. M., '*Interferons: A Primer'*, Academic Press, New York, 1981)). In a recent study of sonophoresis, it has been shown that application of ultrasound at therapeutic frequencies (1 MHz) induces growth and oscillations of air pockets present in the keratinocytes of the SC (a phenomenon known as cavitation). These oscillations disorganize the SC lipid bilayers thereby enhancing transdermal transport. However, application of therapeutic ultrasound does not induce transdermal transport of high-molecular weight proteins.

Transdermal drug delivery offers an advantageous alternative to oral delivery and injections. However, its applications are restricted to only a few drugs because of the extremely low skin permeability to drugs. A variety of approaches have been suggested to enhance transdermal transport of drugs. These include: i) use of chemicals to either modify the skin structure or to increase the drug concentration in the transdermal patch (Junginger, et al. In *"Drug Permeation Enhancement"*; Hsieh, D. S., Eds., pp. 59–90 (Marcel Dekker, Inc. New York 1994); ii) applications of electric fields to create transient transport pathways [electroporation] or to increase the mobility of charged drugs through the skin [iontophoresis], and iii) application of ultrasound [sonophoresis].

U.S. Pat. Nos. 4,309,989 to Fahim and 4,767,402 to Kost, et al., disclose various ways in which ultrasound has been used to achieve transdermal drug delivery.

Sonophoresis has been shown to enhance transdermal transport of various drugs. Although a variety of ultrasound conditions have been used for sonophoresis, the most commonly used conditions correspond to the therapeutic ultrasound (frequency in the range of 1 MHz–3 MHz, and intensity in the range of 0–2 W/cm$^2$) (Kost, In Topical Drug Bioavailability Bioequivalence and Penetration, pp. 91–103, Maibach, H. I., Shah, V. P. (Ed) Plenum Press, New York, 1993; U.S. Pat. No. 4,767,402 to Kost, et al.). It is a common observation that the typical enhancement induced by therapeutic ultrasound is less than tenfold. In many cases, no enhancement of transdermal drug transport has been observed upon ultrasound application. Accordingly, a better selection of ultrasound parameters is needed to induce a higher enhancement of transdermal drug transport by sonophoresis.

About 14 million people in the US are currently suffering from diabetes [1] of which about 1.5 million are treated by insulin administration. the conventional treatment of diabetes involves checking blood glucose levels using finger pricking one or two times a day followed by injections of appropriate amounts of insulin. Although this method provides short term blood glucose control, it offers little patient compliance and results in high rates of long-term diabetic complications such as retinopathy, nephropathy and neuropathy [2]. In order to minimize the long-term complications of diabetes, intensive treatment (insulin delivery three or more times a day accompanied by blood glucose measurements four or more times a day) has been suggested [2]. It has been shown that an intensive treatment of diabetes resulted in about 75% decrease in the risk of developing retinopathy in diabetic patients compared to the conventional therapy. However, intensive treatment of diabetes is not practice by many patients due to pain and discomfort associated with multiple blood glucose measurements and insulin injections. Accordingly, development of a non-invasive blood glucose monitoring method would assist patients adopt intensive treatment.

It is therefore an object of the present invention to provide an improved method for transdermal drug delivery.

It is a further object of the present invention to provide conditions for using sonophoresis for transdermal drug delivery.

It is another object of the present invention to provide an improved, painless method for obtaining a patient sample for measurement of analytes in blood or other body fluids.

SUMMARY OF THE INVENTION

Applications of low-frequency (20 KHz) ultrasound enhances transdermal transport of high-molecular weight proteins. This method includes a simultaneous application of ultrasound and protein on the skin surface in order to deliver therapeutic doses of proteins across the skin. This technique can also be applied with other molecules to be delivered. Delivery can be further enhanced or controlled through the use of carriers for the drugs, such as liposomes or microparticles, using a wide range of ultrasound frequency ranges and intensities. The microparticles are preferably small, and may have surfaces with increased hydrophilicity or lipophilicity to further enhance transport. Examples demonstrate in vitro and in vivo administration of insulin (molecular weight 6,000 D), and in vitro administration of gamma interferon (molecular weight 17,000 D), and erythropoeitin (molecular weight 48,000 D).

It has also been discovered that ultrasound can be used to measure the concentration of analytes in body fluids such as blood or lymph. Examples demonstrate measurement of blood glucose in vitro and in vivo.

BRIEF DESCRIPTION OF THE DRAWINGS

FIGS. 2A–2D are graphs of the time variance of the blood glucose levels of hairless rats (obtained from IFFA, Creto, France, generally about 16 weeks old at the time of the experiment).

DETAILED DESCRIPTION OF THE INVENTION

SONOPHORESIS

As used herein, sonophoresis is the application of ultrasound to the skin on which a drug, most preferably proteinaceous in nature, alone or in combination with a carrier, penetration enhancer, lubricant, or other pharmaceutically acceptable agent for application to the skin, has been applied. Ultrasound is defined as sound at a frequencey of between 20 kHz and 10 MHz, with intensities of between greater than 0 and 3 W/cm$^2$. As used herein, "low frequency" sonophoresis is ultrasound at a frequency that is less than 1 MHz, more typically in the range of 20 to 40 KHz, which is preferably applied in pulses, for example, 100 msec pulses every second at intensities in the range of between zero and 1 W/cm$^2$, more typically between 12.5 mW/cm$^2$ and 225 mW/cm$^2$. Exposures are typically for between 1 and 10 minutes, but may be shorter and/or pulsed. The intensity should not be so high as to raise the skin temperature more than about one to two degrees Centigrade.

Many ultrasound devices are available commercially which can be used in the method described herein. For example, the ultrasonic devices used by dentists to clean teeth have a frequency of between about 25 and 40 KHz. Commercially available portable ultrasound tooth-brushes make use of a small sonicator contained within the toothbrush (Sonex International Corporation). This sonicator is portable and operates on rechargeable batteries. Small pocket-size sonicators carried by patients and used to "inject" drugs whenever required could be readily adapted from these devices. In addition, these devices could be potentially combined with sensors that can monitor drug concentrations in the blood to formulate a self-controlled drug (insulin, for example) delivery method that can potentially eliminate the attention required by the patient.

Devices typically used for therapeutic or diagnostic ultrasound operate at a frequency of between 1.6 and 10 MHz. These devices can also be modified for use at lower frequencies.

DRUG DELIVERY

Drugs to be Administered

Drugs to be administered include a variety of bioactive agents, but are preferably proteins or peptides. Specific examples include insulin, erythropoietin, and interferon. Other materials, including nucleic acid molecules such as antisense and genes encoding therapeutic proteins, synthetic organic and inorganic molecules including antiinflammatories, antivirals, antifungals, antibiotics, local anesthetics, and saccharides, can also be administered.

The drug will typically be administered in an appropriate pharmaceutically acceptable carrier having an absorption coefficient similar to water, such as an aqueous gel. Alternatively, a transdermal patch such as the one described in the examples can be used as a carrier. Drug can be administered in a gel, ointment, lotion, suspension or patch, which can incorporate anyone of the foregoing.

Encapsulation in Delivery Devices

In one embodiment, the drug is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. The microparticles can have diameters of between 0.001 and 100 microns, although a diameter of less than 10 microns is preferred. The microparticles can be coated or formed of materials enhancing penetration, such as lipophilic materials or hydrophilic molecules, for example, polyalkylene oxide polymers and conjugates, such as polyethylene glycol. Liposome are also commercially available.

Administration of Drug

The drug is preferably administered to the skin at a site selected based on convenience to the patient as well as maximum drug penetration. For example, the arm, thigh, or stomach represent areas of relatively thin skin and high surface area, while the hands and feet are uneven and calloused. In the preferred embodiment, drug is applied to the site and ultrasound applied immediately thereafter.

Based on these calculations and the data in the following examples, one can calculate the required dosage and application regime for treatment of a patient, as follows. A typical diabetic patient (70 Kg weight) takes about 12 Units of insulin three times a day (total dose of about 36 Units per day: cited in 'World Book of Diabetes in Practice' Krall, L. P. (Ed), Elsvier, 1988). If each insulin dose was to be delivered by sonophoresis in 1 hour, the required transdermal flux would be 12 U/hour. Note that 1 unit (1 U) of insulin corresponds approximately to 40 mg of insulin. The transdermal patch area used in these calculations is 40 cm$^2$ (the area of a transdermal Fentanyl patch [ALZA Corporation]). The donor concentrations used in these calculations are 100 U/ml in the case of insulin (commercially available insulin solution [Humulin]), $3 \times 10^7$ in the case of γ-interferon (typical concentration of interferon solution recommended by Genzyme Corporation), and $3 \times 10^5$ U/ml in the case of erythropoeitin [Davis J., Arakawa T., Strickland T., Yphantis D., Biochemistry, 2633–2638, 1987].

A typical γ-interferon dose given each time to patients suffering from cancer or viral infections is about $5 \times 10^6$ U [(i) Grups J. W., Frohmuller H. G., Br. J. Med., 1989, 64 (3): 218–220, (ii) Parkin J. M., Eales L., Galazka A., Pinching A., Br. Med. J., 1987, 294: 1185–1186.] Similar doses of α-interferon and β-interferon have also been shown to enhance the immune response of patients suffering from viral infections and cancer (cited in 'Clinical Applications of interferons and their inducers', Ed. Stringfellow D., Marcel Dekker, New York, 1986). If this interferon dose was to be given by sonophoresis in 1 hour, the required transdermal flux would be $5 \times 10^6$ U/hour. Note that 1 unit of γ-interferon corresponds approximately to 1 pg of γ-interferon.

A typical daily erythropoeitin dose given subcutaneously to anemic patients is about 400 U (cited in "Subcutaneous Erythropoeitin", Bommer J., Ritz E., Weinreich T., Bommer G., Ziegler T., Lancet, 406, 1988). If this dose was to be delivered in three steps, each involving sonophoresis for 1 hour, the transdermal flux required would be about 140 U/hour. Note that 1 unit of erythropoeitin corresponds approximately to 7.6 nanograms of erythropoeitin.

An optimal selection of ultrasound parameters, such as frequency, pulse length, intensity, as well as of non-ultrasonic parameters, such as ultrasound coupling medium, can be conducted to ensure a safe and efficacious application using the guidelines disclosed herein as applied by one of ordinary skill in the art.

MEASUREMENT OF ANALYTES

Analytes to be Measured

A variety of analytes are routinely measured in the blood and/or lymph. Measurements usually require making a puncture in order to withdraw sample. Examples of typical analytes that can be measured include blood sugar (glucose), cholesterol, bilirubin, creatine, various metabolic enzymes, hemoglobin, heparin, vitamin K or other clotting factors, uric acid, carcinoembryonic antigen or other tumor antigens, and various reproductive hormones such as those associated with ovulation or pregnancy.

Measurement of Analytes

The ultrasound is applied to the skin at the site where the sample is to be collected. A reservoir or collecting container is applied to the site for collection of the sample, which is then measured using standard techniques. The ultrasound conditions are optimized as in the case for drug delivery, to maximize analyte recovery, while maintaining the relative levels of the analyte to other components of the sample.

The present invention will be further understood by reference to the following non-limiting examples.

EXAMPLE 1

In Vitro Administration of Insulin

Materials and methods: In vivo as well as in vitro experiments were performed to study the effect of low-frequency ultrasound on the transport of insulin across the skin. In vitro experiments were performed using human cadaver skin. The skin was heat stripped by keeping it in water at 60° C. for two minutes followed by the removal of the epidermis. It was then stored at 4° C. in a humidified chamber. A piece of epidermis was taken out from the chamber prior to the experiments and was mounted on the Franz diffusion cell (Crown Bioscientific Co.) which consists of two compartments, the donor and the receiver compartment. A Franz Diffusion Cell consists of two compartments, a donor and a receiver compartment. The human cadaver epidermis (separated from the dermis by heat-treatment) is mounted between the two compartments and is supported by a Nylon mesh (Tetko Inc.) to avoid any damage. The skin was supported by a nylon mesh (Tetko Inc.) in order to a mimic the fact the skin in vivo is supported by mechanically strong dermis. The compartments were then clamped together. The receiver compartment was filled with 2%. BSA (Sigma Chemicals) solution in PBS (Sigma Chemicals) and the donor solution was filled with 100 U/ml solution of human recombinant insulin (Humulin Regular). The ultrasound intensity, I, (Spatial Average Temporal Peak) was calculated from the values of the acoustic pressure amplitude, P, measured using a hydrophone (Bruel and Kjaer) using the equation, $I=P^2/2\rho c$, where $\rho$ is the water density (1 gm/ml), and c is the velocity of ultrasound in water [1500 m/s].

Ultrasound was turned ON at a frequency of 20 KHz, an intensity varying in the range of 0 to 1 W/cm² and 10% duty cycle. Samples (200 µl) were taken from the receiver compartment every hour to measure the concentration of insulin in the receiver compartment. The samples were immediately frozen and were stored at −20° C. till they were analyzed by RIA (Linco Research Co.). Ultrasound was typically applied for 4 hours and was then turned OFF. Transdermal insulin flux was followed for next two hours.

Figure 1A:
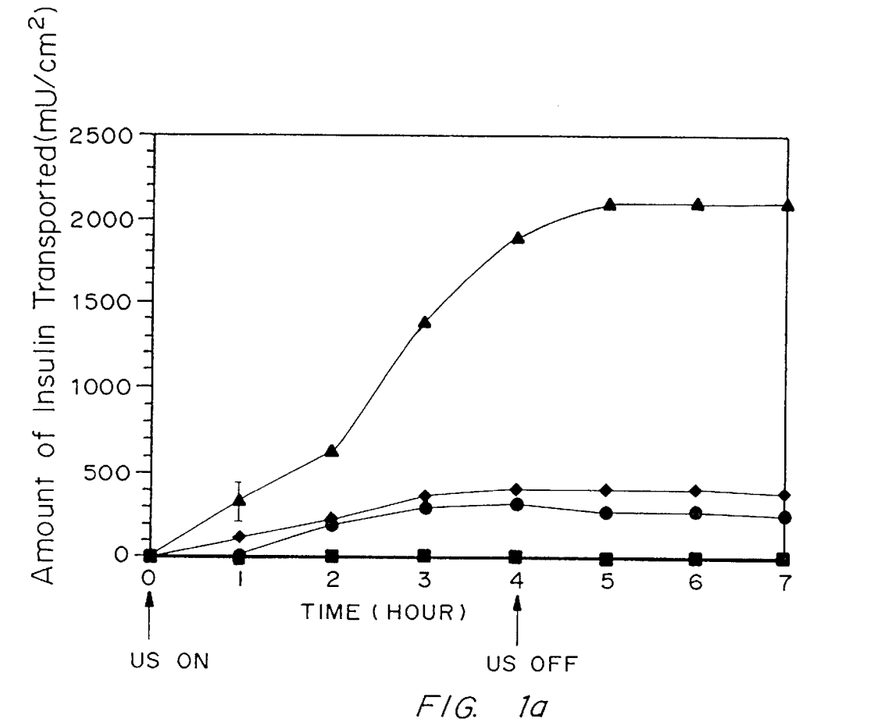
FIG. 1A is a graph of the amount of insulin transported across human skin (in vitro) in the presence of ultrasound (20 KHz, 100 msec pulses applied every second) at various intensities (■—12.5 mW/cm$^2$, ♦—62.5 mW/cm$^2$, ●—125 mW/cm$^2$, and ▲—225 mW/cm$^2$). (n=3–4, error bars indicate SD (Standard Deviation))
Figure 1B:
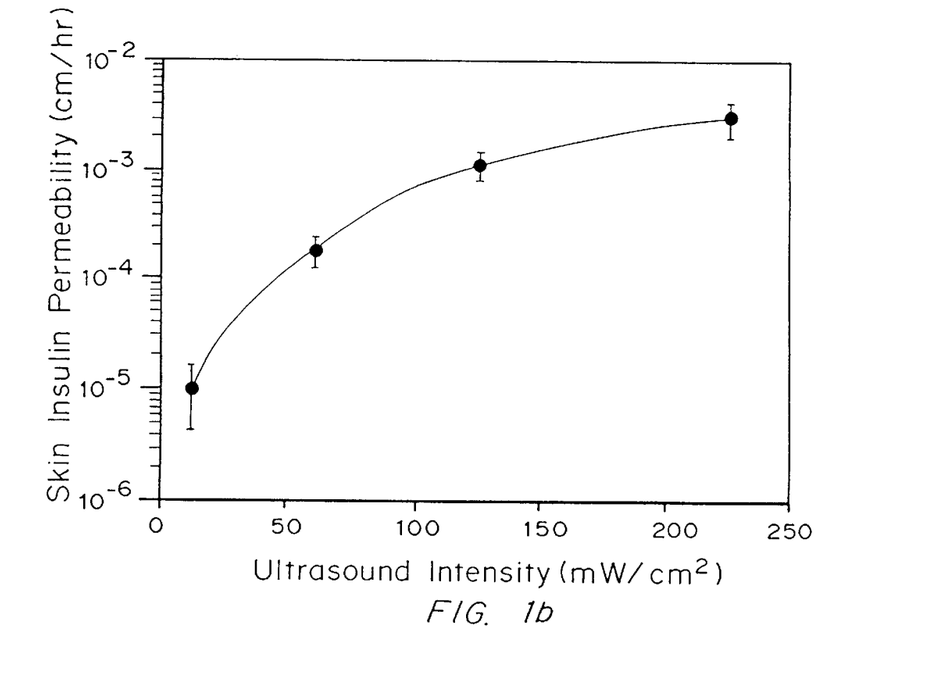
FIG. 1B is a graph of the variation of the transdermal insulin permeability (in vitro) with ultrasound intensity (20 KHz, 100 msec pulses applied every second). (n=3–4, error bars indicate SD.) Note that the skin is impermeable to insulin at an ultrasound intensity =○.

Results: The results are shown in FIGS. 1A and 1B and demonstrate that substantially greater transfer of protein through the skin occurs in the presence of ultrasound. FIGS. 1A and 1B show the variation of transdermal insulin flux across the human skin in vitro. Ultrasound (20 KHz, 125 mW/cm², 10%) was turned ON at time zero. The insulin flux increased from below the detection limit to a value of about 100 mU/cm²/hr in about 1 hour and stayed almost constant around that value as long as ultrasound was ON. Upon turning ultrasound OFF, the insulin flux decreases and achieves a value below our detection limit within 2 hours after turning ultrasound OFF. The skin permeabilities to insulin at various ultrasound intensities were calculated from the amount of insulin transported during the first hour of ultrasound exposure and are shown in FIG. 1B. The sonophoretic permeability varies nearly exponentially with ultrasound intensity, probably due to a highly non-linear dependence of cavitation on ultrasound intensity (Apfel, R. E., *IEEE Trans. Ultrason. Ferroelectrics Freq. Control* 1986, UFFC-33, 139).

Application of ultrasound under these conditions did not appear to cause any permanent loss of the barrier properties of the skin. The transdermal insulin flux (proportional to the slope of the curves shown in FIG. 1A) three hours after turning ultrasound OFF was statistically insignificant. To further assess the recovery of the skin barrier properties after sonophoresis, water transport was measured through the skin during and after ultrasound exposure (20 KHz, 125 mW/cm², 100 msec pulses applied every second). Transdermal water transport was measured using the same set-up utilized in the insulin experiments, except that the donor compartment was filled with a 1 µCi/ml solution of radio-labelled water ($^3$H). The concentration of water in the receiver compartment was measured using, a scintillation counter. During sonophoresis, a water permeability enhancement of 100-fold was observed, of which about 94 (±3)% was recovered within 2 hours after turning ultrasound OFF and 98 (±1)% was recovered within 15 hours. These results suggest that application of ultrasound does not induce any long-lasting loss of the skin barrier properties.

With a transdermal insulin flux of 100 mU/cm²/hr, it should be possible to deliver therapeutic doses of insulin transdermally. Specifically, an insulin dose of about 13 U/h (a dose comparable to the estimated dose required by a diabetic patient if insulin is administered at a controlled rate) could be delivered from a patch having an area of 100 cm². Accordingly, ultrasound intensity should be useful to control transdermal insulin delivery.

EXAMPLE 2

In Vitro Transfer of Other Proteins

Methods and materials: The passive skin permeability to high-molecular weight proteins, including those mentioned above, is essentially zero (below the detection limit). To assess whether application of ultrasound enhances transdermal protein flux, the skin permeability to these proteins in the presence of ultrasound in vitro across human cadaver epidermis in a Franz Diffusion Cell (Crown Glass Company) was measured. In separate experiments, the donor compartment of the diffusion cell was filled with a solution of insulin (100 U/ml, Humulin Regular, Eli Lilly), γ-interferon (2500 U/ml, Genzyme Corp.), or erythropoeitin (400 U/ml, Amgen Corp.). Ultrasound (20 KHz, 100 msec pulses applied every second) was applied at intensities in the range of 12.5 mW/cm²-225 mW/cm² for 4 hours using an ultrasound transducer (VCX 400, Sonics and Materials) which was immersed in the donor solution. The transducer having an area of about 1 cm² was oriented perpendicular to the skin and placed at a distance of 1 cm from the skin. The concentration of proteins in the receiver compartment was measured every hour either by RIA or ELISA. The insulin concentration in the receiver compartment was measured every hour by Radioimmuno Assay (performed at Linco Research Inc., St. Charles). The γ-interferon concentration was measured using ELISA methods developed by Endogen Inc, and the erythropoeitin concentration was measured by ELISA (performed at ARUP, Salt Lake City). Skin permeabilities to proteins were calculated using the transdermal fluxes measured during the first hour. The transdermal flux can be calculated using the equation, $J = \Delta M/\Delta t$, where $\Delta M$ is the amount of protein transported per unit skin area during time $\Delta t$. The skin permeabilities, P, can be calculated from the transdermal flux, J, during the first hour of ultrasound application using the equation, $P = J/\Delta C$, where $\Delta C$ is the concentration difference across the skin.

Results: Ultrasound application induces significant transdermal permeation of insulin, γ-interferon, and erythropoeitin. As demonstrated in Example 1, the human skin permeability at an ultrasound intensity of 225 mW/cm² is $3.3 \times 10^{-3}$ (±35%) cm/h to insulin. The permeability to γ-interferon under similar ultrasound conditions is $8 \times 10^{-4}$ (±22%) cm/h, and that to erythropoeitin is $9.8 \times 10^{-6}$ (±40%) cm/h. With these skin permeabilities, it should be possible to deliver these proteins transdermally at a therapeutically relevant rate. For example, one could deliver an insulin dose of about 12 U/h (a dose given three times a day to a diabetic patient) from a transdermal patch having an area of 40 cm² containing insulin at a concentration of 100 U/ml. In other words, one hour of sonophoresis performed three times a day could deliver the required daily dose of insulin to a diabetic patient. Similarly, a γ-interferon dose of about $5 \times 10^6$ U/h (a daily dose required to enhance the immune response of patients suffering from viral infection or cancer), and an erythropoeitin dose of about 140 U/h (a dose that may be given three times a day to patients suffering from severe anemia) may be delivered from a similar patch by application of ultrasound. The ability of sonophoresis to deliver other macromolecules may be estimated based on their sonophoretic skin permeability which needs to be measured experimentally (generally decreases with increasing molecular size) and the required therapeutic dose of these macromolecules.

EXAMPLE 3

In Vivo Administration of Insulin

To assess the efficacy of ultrasound in enhancing transdermal flux in an in vivo model, insulin sonophoresis experiments were performed on hairless rats. The transport properties of hairless rat and hairless mouse skin have been shown to resemble those of human skin. The passive permeability of the hairless rat skin to many compounds is within a factor of 2–5 of the human skin permeability.

(Morimoto, Y., Hatanaka, T., Sugibayashi, K., Omiya, H., *J. Pharm. Pharmacol.,* 44:634–639., Wester, R., Maibach, H. I., In Topical Drug Bioavailability Bioequivalence and Penetration, Maibach, H. I., Shah, V. P. (Ed) pages 333–347, Plenum Press, New York, 1993).

Materials and Methods: In vivo experiments were performed using hairless rats (Charles River). The rats were kept in quarantine to insure good health. On the day of experiment, they were taken out of the cages, anesthetized using a mixture of ketamine (90 mg/kg) and xylazine (10 mg/kg). After about an hour into anesthesia, a glass chamber was glued to the back of the rat using superglue (Permeabond). The glass chamber was filled with 100 U/ml solution of insulin and ultrasound (frequency of 20 KHz, intensity in the range of 0 to 1 W/cm$^2$, 100 msec pulses applied every second) was applied. The blood glucose level was measured every 30 minutes. Ultrasound was typically turned OFF after 1 hour, although the measurements of the blood glucose were continued for the next three hours.

The electrical resistance of the skin prior to each sonophoresis experiment was measured to ensure that the epidermis was not damaged. The epidermis is considered to be damaged if the initial specific epidermis resistance is less than 10 KΩ-cm$^2$ [Rossel J., Colominas J., Riu P, Pallas-Arery, Webster J., IEEE Trans. Biomed. Eng. 35: 649–651, 1988].

Histology samples from the area exposed to ultrasound were taken after the experiment was done and were stained using eosin and hematoxylin (Debora Heart and Lung Center). The histological studies of the hairless rat skin exposed to ultrasound were performed at Deborah Heart and Lung Institute, New Jersey. The skin samples, those exposed to ultrasound as well as those unexposed to ultrasound (controls), were stained with hematoxylin and eosin. These samples were later observed under a light microscope (40-fold magnification) to assess for possible structural damage. Five control skin samples and 20 skin samples exposed to ultrasound (5 samples corresponding to each ultrasound intensity in the range of 12.5 mW/cm$^2$ to 225 mW/cm$^2$) were analyzed.

Results: Application of ultrasound (20 KHz, 125 mW/cm$^2$, 100 msec pulses applied every second) enhances insulin transport across the hairless rat skin in vivo. Simultaneous application of insulin and ultrasound decreases the blood glucose level of a diabetic rat from a high diabetic value (400 mg/dl) to the normal value (200 mg/dl) in 30 minutes.

Preliminary histological studies to assess the safety of low-frequency ultrasound as a transdermal transport enhancer were also conducted. The results indicated no damage to the skin as well as to the underlying parts of the skin exposed to ultrasound at an intensity up to 225 mW/cm$^2$.

Figure 2A:
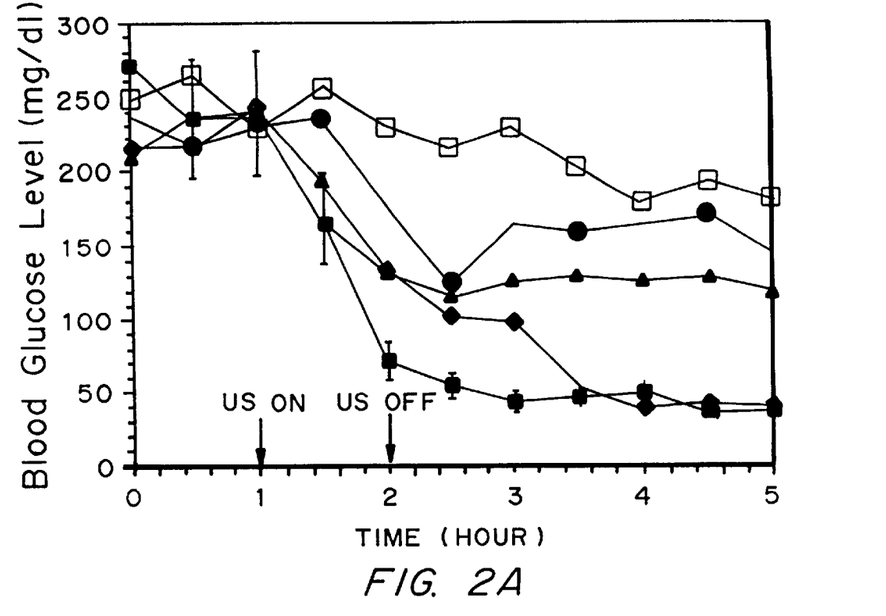
FIG. 2A is the blood glucose levels upon 1 hour insulin-ultrasound treatment (ultrasound was turned ON at 1 hour and turned OFF at 2 hours) at four different intensities (□—Control (n=4), ●—12.5 mW/cm$^2$ (n=3), ▲—62.5 mW/cm$^2$ (n=3), ♦—125 mW/cm$^2$ (n=3), and ■—225 mW/cm$^2$ (n=5)).

FIG. 2A shows the blood glucose level of hairless rats upon a 1 hour insulin-ultrasound treatment (20 KHz, 100 msec pulses applied every second at intensities of 0 to 225 mW/cm$^2$. An intensity dependent decrease in the blood glucose level is observed upon ultrasound application, indicating that low-frequency sonophoresis can effectively deliver intensity-dependent insulin doses across hairless rat skin.

Figure 2B:
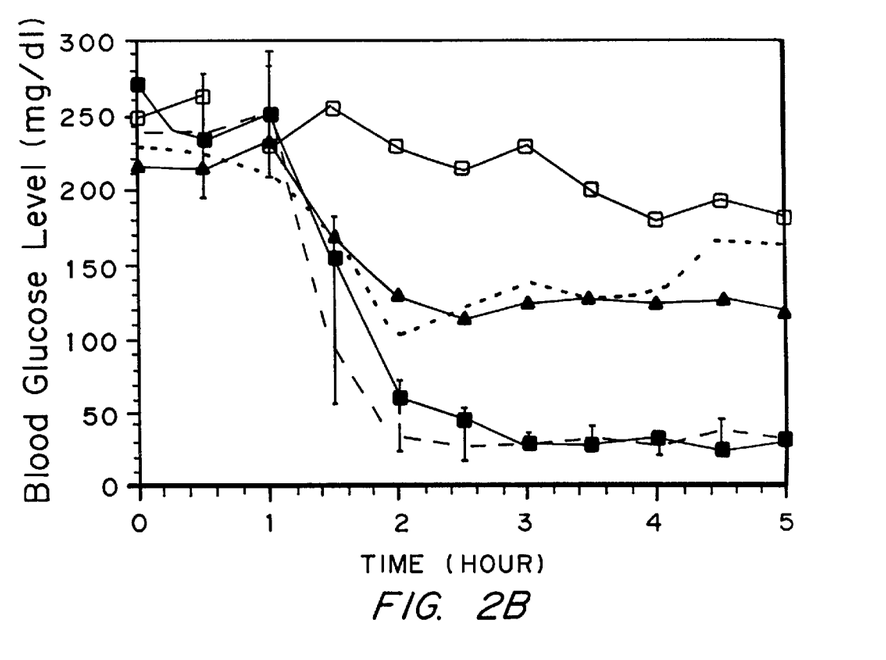
FIG. 2B is a graph comparing the blood glucose level of rats treated for 1 hour (from time 1 to 2 hours) with sonophoresis at two intensities (▲—62.5 mW/cm$^2$ (n=3), ■—225 mW/cm$^2$(n=5)) and those treated with a single subcutaneous injection at time 1 hour (dashed line—1 U (n=3), dotted line—100 mU (n=3). A typical rat weighed about 400 g. The control is indicated by (□) (error bars (SD) are shown on one set of data for subcutaneous as well as for sonophoresis data.) FIG. 2C is a graph of the time variation of blood glucose levels of hairless rats exposed to ultrasound (20 KHz, 225 mW/cm$^2$, 100 msec pulses applied every second) for different exposure times. Ultrasound was turned ON at 1 hour (indicated by the arrow) and was turned OFF after: 1 minute (●) (n=3), 10 minutes (▲) (n=3), and 1 hour (■) (n=5). The control is indicated by (□) (error bars (SD) are shown on one set of data).

To estimate the amount of insulin penetrating the hairless rat skin during sonophoresis at the various intensities reported in FIG. 2A, various known amounts of insulin in the range of 0 to 1 U subcutaneously (most commonly used method of insulin administration today) in normal rats. The blood glucose levels of these rats were then compared with those of the normal rats undergoing sonophoresis. Subcutaneous injection of 100 mU and 1 U of insulin induced a decrease in the blood glucose level similar to that induced by sonophoresis using intensities of 62.5 mW/cm$^2$ and 225 mW/cm$^2$ respectively (see FIG. 2B). These results suggest that sonophoresis delivers intensity dependent insulin doses across the skin approximately in the range of 0 to 1 U (through an area of about 3 cm$^2$).

Figure 2C:
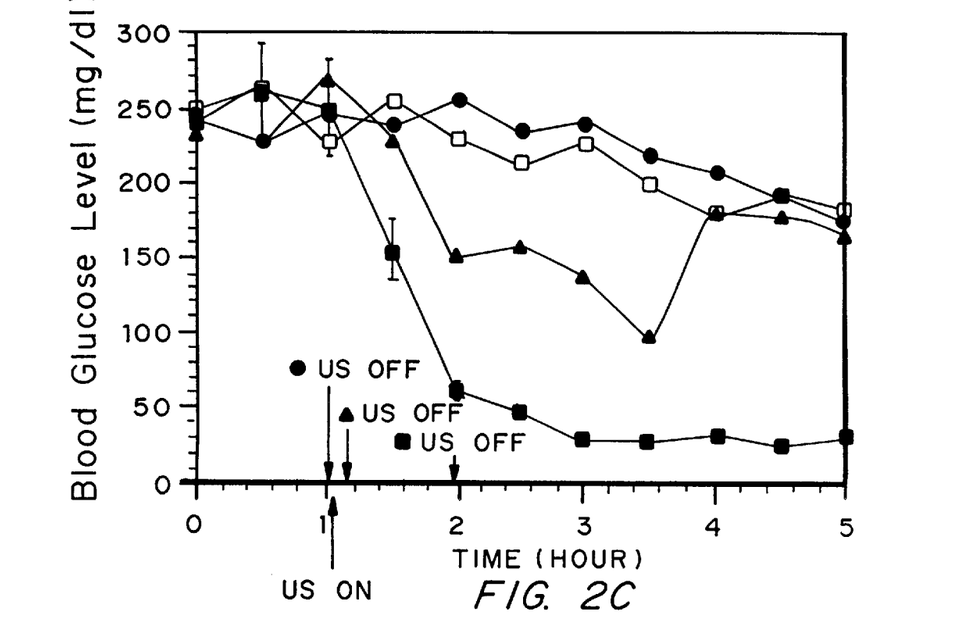

In order to estimate the dependence of the amount of insulin delivered on ultrasound exposure time (in vivo), insulin-sonophoresis experiments (20 KHz, 225 W/cm$^2$, 100 msec pulses applied every second) were performed on normal rats for different exposure times in the range of 1 minute to 1 hour. FIG. 2C shows that while a 1 hour exposure decreases blood glucose level from about 250 mg/dl to about 30 mg/dl, a 10 minute exposure to ultrasound reduces the blood glucose level of hairless rats from about 250 mg/dl to about 150 mg/dl. This result, when compared with the data reported in FIG. 2B, suggests that while a 1 hour ultrasound exposure delivers about 1 U of insulin, a 10 minute ultrasound application (225 mW/cm$^2$) delivers about 100 mU through an area of 3 cm$^2$.

Figure 2D:
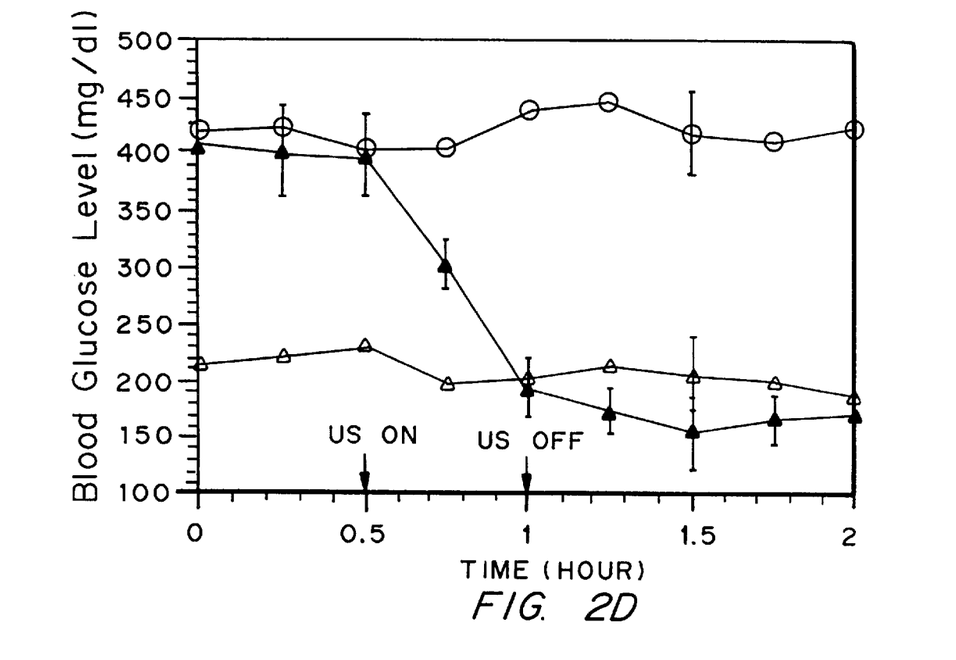
FIG. 2D is a graph of the time variation of blood glucose levels of diabetic hairless rats upon a 30 minute insulin-ultrasound treatment (ultrasound was turned ON at 0.5 hour and turned OFF at 1 hour). (0—Diabetic Rats, Δ—Normal Rats, ▲—Diabetic Rats with insulin-ultrasound treatment.) (n=4 per experiment, error bars indicate SD).

Additional experiments were performed to assess whether application of ultrasound can induce sufficient insulin transport across the skin of a diabetic hairless rat so that its blood glucose level becomes comparable to that of normal hairless rats. FIG. 2D shows blood glucose levels of diabetic rats during ultrasound-insulin treatment. Insulin-ultrasound treatment (20 KHz, 225 mW/cm$^2$, 100 msec pulses applied every second) reduces the blood glucose level of diabetic hairless rats from about 400 mg/dl to 200 mg/dl (the blood glucose level of normal rats) in 30 minutes. A corresponding change in the plasma insulin levels was observed during sonophoresis. Normal hairless rats were found to possess a plasma insulin level of 101±31 picomolar, while diabetic hairless rats were found to possess a value below the assay detection limit (34 picomolar). During sonophoresis, the levels of transdermally delivered human insulin in rat plasma reached a value of 77 (±28) picomolar after 30 minutes, and a value of 178 (±84) picomolar after 1 hour. No significant change in the plasma concentration of indigenous rat insulin was observed during sonophoresis.

The histology studies indicated no physical damage in the skin or in the underlying muscle tissues exposed to ultrasound at all the intensities used in the experiments described above. The regions of hairless rat's epidermis exposed to ultrasound were intact.

EXAMPLE 4

Transdermal Glucose Extraction by Sonophoresis In Vitro

Application of low-frequency ultrasound can be used to extract glucose across the skin, thus making non-invasive transdermal blood glucose monitoring potentially feasible.

Materials and Methods

In Vitro Transdermal Transport Measurements:

Transdermal transport of a $^{14}$C labeled (New England Nuclear) as well as non-labeled (Sigma Chemicals) was studied in the presence as well as in the absence of low-frequency ultrasound. The permeability experiments were performed in vitro using human cadaver skin obtained from local hospitals. The skin was heat stripped by keeping the full-thickness skin in water at 60° C. for two minutes followed by the removal of the epidermis. The skin was then stored at 4° C. in a humidified chamber for up to 2 weeks. A piece of the epidermis was taken out from the chamber prior to the experiments and was mounted on a Franz diffusion cell (Crown Glass Co., FDC 200). The Franz diffusion cell consists of two compartments, the donor and the receiver compartments, with the stratum corneum facing the donor compartment. The skin was supported by a nylon mesh (Tetko, Inc.) to avoid any damage due to possible mechanical oscillations upon ultrasound application. The donor and receiver compartments were then clamped. The receiver compartment was filled Phosphate Buffer Saline (PBS, phosphate concentration=0.01M, NaCl concentration=0.137M) (Sigma Chemicals Co.) The donor compartment was filled with a solution of either radiolabelled glucose (1 mCi/ml) or non-labeled glucose (concentration in the range of 50 mg/dL to 300 mg/dL) in separate experiments. The concentration of the permeant in the receiver compartment was measured every 5 minutes using a scintillation counter (model 2000 CA, Packard) in the case of radiolabelled glucose and using a commercially available kit (Sigma Chemicals) in the case of unlabeled glucose.

Ultrasound was applied using a sonicator (VCX 400, Sonics and Materials) operating at a frequency of 20 KHz. The ultrasound intensity was measured using a hydrophone (Model 8106, Bruel and Kjaer).

RESULTS

Figure 3A:
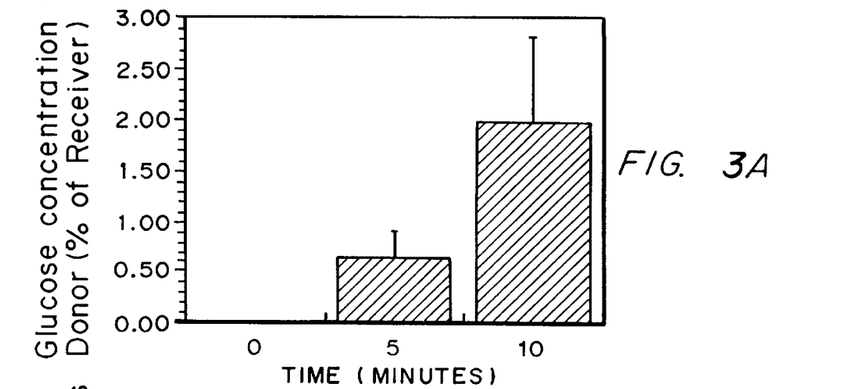
FIG. 3A is a graph of glucose concentration in the donor compartment (measured as percent of received glucose) over time (minutes) in an in vitro system.

FIG. 3A shows the glucose concentration in the donor compartment (represented as percent of the glucose concentration in the receiver compartment) attained at different times during transdermal glucose extraction experiment. The figure shows that even a 5 minute ultrasound application (20 KHz, 125 mW/cm$^2$, continuous) results in a significant glucose transport across human skin in vitro. Specifically, the glucose concentration in the donor compartment after 5 minutes of sonophoresis is about 0.5% of that in the receiver compartment. After 10 minutes, the glucose concentration in the donor compartment was about 2% of that in the receiver compartment. The glucose concentration in this range can be measured in situ using glucose sensing electrodes, and can be calibrated to indicate actual blood glucose levels. The amount of glucose extracted by sonophoresis under a given condition varies in the case of skin obtained from different donors (typical variation 40% (SD)). However, the variation in the case of skin obtained from the same donor is only about 13%, thus indicating that it should be possible to achieve reliable estimates of glucose concentrations based on transdermal glucose extraction after performing calibration in vivo on the patient's skin.

Figure 3B:
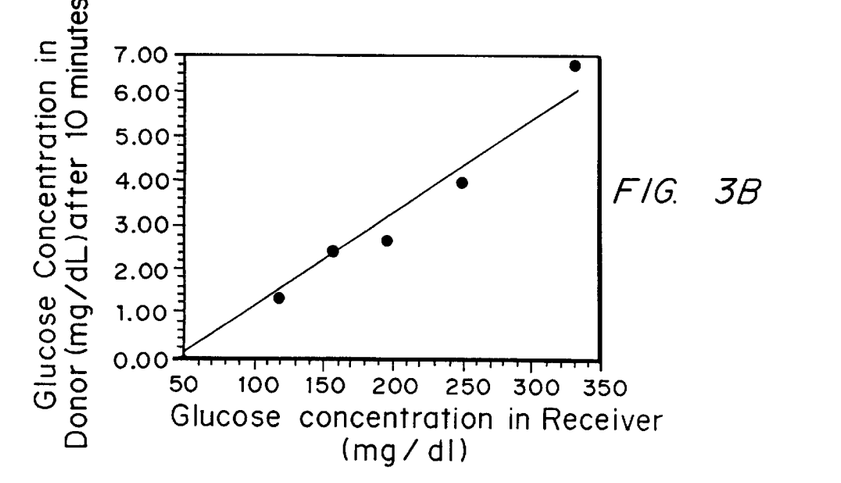
FIG. 3B is a graph of glucose concentration in the donor compartment (mg/dl) after ten minutes as a function of glucose concentration in the receiver compartment (mg/dl).

Additional experiments were performed to assess whether the amount of glucose transported by sonophoresis is proportional to the glucose concentration in the receiver compartment. In separate experiments, glucose concentration in the receiver solution was varied from 50 mg/dL to 350 mg/dL (typical variation in the blood glucose level of a diabetic patient) and performed sonophoresis using ultrasound (20 KHz, 125 mW/cm$^2$, continuous) for 10 minutes. FIG. 3B shows that the glucose concentration attained in the donor compartment 10 minutes after sonophoresis (represented as percentage of the glucose concentration in the receiver compartment) increased from 0.5 mg/dL to 6.5 mg/dL as glucose concentration in the receiver compartment increased from 50 mg/dL to 350 mg/dL. The line shown in FIG. 3B represents the best fit. These results show that the amount of glucose extracted across human skin is proportional to the glucose concentration under the skin, thus indicating that transdermal glucose extraction by sonophoresis could be potentially used for blood glucose measurement.

EXAMPLE 5

Transdermal Glucose Extraction by Sonophoresis In Vivo

Materials and Methods

In Vivo Transport Experiments:

In vivo experiments were performed to assess the efficacy of sonophoresis across living skin. Hairless rats (Charles River, 8–12 weeks old, either sex) were used as an animal model for these studies, since it has been shown that the transport properties of hairless rat skin is comparable to that of human skin (Wester, *Animal Models for Percutaneous Absorption, In Topical Drug Bioavailability, Bioequivalence, and Penetration,* Shah V.P. and M.H.L., eds. (Plenum Press, NY 1993)). The hairless rats were anesthetized with a mixture of ketamine (60 mg/kg) and xylazine (10 mg/kg). After about an hour in anesthesia, a flanged glass cylinder (Crown Glass Company, diameter 20 mm, height 2 cm) was glued on the rat's back using a minimal amount of superglue (Permabond International) or vacuum grease (Dow Chemicals) on the outer edge of the flange. The center of the cylinder was located about 3 cm from the rear end of the rat. This particular site was chosen to avoid application of ultrasound directly on a sharp bone close to the body surface, which otherwise might have caused damage to the blood capillaries near the edge of the bone. The cylinder was filled with PBS (phosphate concentration=0.01M, NaCl concentration=0.137M) (Sigma Chemicals Co.). Ultrasound (20 KHz, 125 mW/cm$^2$, continuous) was applied for 1 minute by immersing the transducer in the donor solution. The concentration of glucose in PBS was measured using an assay kit (Sigma Chemicals).

RESULTS

Figure 4:
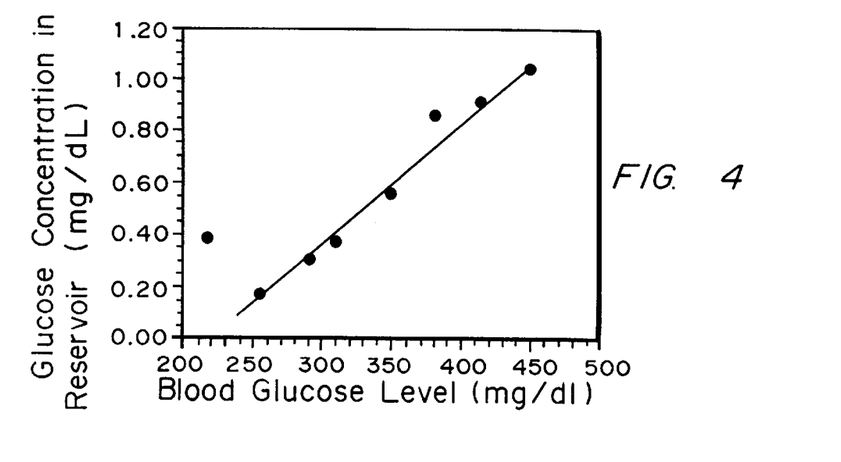
FIG. 4 is a graph of the glucose concentration extracted transdermally by sonophoresis at 20 KHz, 62.5 mW/cm$^2$, continuous, 1 minute) in vivo with the blood glucose level (mg/dl) of hairless rats.

In vivo experiments were performed using normal as well as diabetic hairless rats to assess whether low-frequency ultrasound extracts glucose across living skin. FIG. 4 shows that application of ultrasound (20 KHz, 62.5, continuous, 1 minute, applied on side of the stomach) induces glucose extraction by an amount proportional to the rat blood glucose level. Specifically, the glucose concentration in the reservoir after extraction increased from 0.2 mg/dL to 1 mg/dL as the rat blood glucose level increased from about 200 mg/dL to 450 mg/dL in separate experiments. These results indicate that calibration curves relating glucose extracted transdermally and blood glucose level can be used for non-invasive blood glucose measurements.

Modifications and variations of the method for transdermal drug delivery enhancement using sonophoresis described herein will be obvious to those skilled in the art and are intended to be encompassed by the following claims.

We claim:

1. A method for enhancing delivery of a drug across the skin comprising applying the drug encapsulated in a liposome or polymeric microparticle to the skin in a pharmaceutically acceptable carrier having an absorbance coefficient equivalent to water and applying ultrasound at a frequency of between 20 kHz and less than 10 MHz at an intensity not causing any irreversible skin damage for a period of time effective to deliver the drug encapsulated in the liposome or microparticle across the skin in a desired drug dosage.

2. The method of claim 1 wherein the drug is a peptide or protein.

3. The method of claim 1 wherein the encapsulating material is a liposome.

4. The method of claim 1 wherein the encapsulating material is a polymeric microparticle.

5. The method of claim 4 wherein the microparticle is coated with a lipophilic or hydrophilic material enhancing transdermal penetration.

6. The method of claim 5 wherein the material is a hydrophilic molecule coupled to a synthetic biodegradable polymer forming the microparticle.

7. The method of claim 1 wherein the frequency is between 20 and 45 kHz.

8. The method of claim 1 wherein the intensity is between zero and 1 $W/cm^2$.

9. The method of claim 5 wherein the intensity is between 12.5 $mW/cm^2$ and 225 $mW/cm^2$.

* * * * *